United States Patent
Troxell et al.

(10) Patent No.: US 11,110,239 B2
(45) Date of Patent: Sep. 7, 2021

(54) COUGH DETECTION IN A RESPIRATORY SUPPORT SYSTEM

(71) Applicant: KONINKLIJKE PHILIPS N.V., Eindhoven (NL)

(72) Inventors: David Troxell, Los Osos, CA (US); William Anthony Truschel, Oakmont, PA (US)

(73) Assignee: Koninklijke Philips N.V., Eindhoven (NL)

(*) Notice: Subject to any disclaimer, the term of this patent is extended or adjusted under 35 U.S.C. 154(b) by 469 days.

(21) Appl. No.: 16/191,594

(22) Filed: Nov. 15, 2018

(65) Prior Publication Data
US 2019/0151585 A1    May 23, 2019

Related U.S. Application Data

(60) Provisional application No. 62/587,602, filed on Nov. 17, 2017.

(51) Int. Cl.
*A61M 16/00* (2006.01)
*A61B 5/00* (2006.01)
(Continued)

(52) U.S. Cl.
CPC .......... *A61M 16/026* (2017.08); *A61B 5/087* (2013.01); *A61B 5/0823* (2013.01);
(Continued)

(58) Field of Classification Search
CPC ............ A61M 16/026; A61M 16/0006; A61B 5/7282; A61B 5/0823; A61B 5/087; A61B 2562/0247; A61B 5/0816
See application file for complete search history.

(56) References Cited

U.S. PATENT DOCUMENTS 8,603,006 B2    12/2013    Mulqueeny
2007/0215155 A1    9/2007    Marx
(Continued)

FOREIGN PATENT DOCUMENTS

| WO | WO2015138924 A1 | 9/2015 |
| WO | 2016103116 A1 | 6/2016 |
| WO | WO2017032882 A1 | 3/2017 |

OTHER PUBLICATIONS

Sundar, K.M. et al., "Chronic Cough and OSA: A New Association?", JCSM, Journal of Clinical Sleep Medicine, vol. 7, No. 6, pp. 669-677, 2011.
(Continued)

*Primary Examiner* — Margaret M Luarca
(74) *Attorney, Agent, or Firm* — Daniel H. Brean

(57) ABSTRACT

The present disclosure pertains to a pressure support system configured to identify respiratory events of a subject. The system is configured to produce and analyze signals pertaining to one or more parameters of the pressurized flow of breathable gas to identify respiratory events. The respiratory events may include coughs and/or other respiratory events. The parameters may comprise a pressure, flow and/or volume of the pressurized flow of breathable gas. In some embodiments, cough detection may be based on a vibration in pressure, a negative spike in flow, a cessation in flow, and/or a large insufflation. In some embodiments, the system comprises one or more of a pressure generator, a subject interface, one or more sensors, a processor, a user interface, electronic storage, and/or other components.

15 Claims, 6 Drawing Sheets

(51) Int. Cl.
  *A61B 5/08* (2006.01)
  *A61B 5/087* (2006.01)
  *A61M 16/08* (2006.01)
(52) U.S. Cl.
  CPC ........... *A61B 5/7282* (2013.01); *A61M 16/08* (2013.01); *A61B 5/0816* (2013.01); *A61B 2562/0247* (2013.01); *A61M 16/0006* (2014.02); *A61M 2016/0027* (2013.01); *A61M 2016/0033* (2013.01); *A61M 2205/3368* (2013.01); *A61M 2205/502* (2013.01)

(56) References Cited

U.S. PATENT DOCUMENTS

| | | | |
|---|---|---|---|
| 2007/0276278 A1 | 11/2007 | Coyle | |
| 2011/0087079 A1 | 4/2011 | Aarts | |
| 2012/0302921 A1 | 11/2012 | Gavriely | |
| 2014/0373844 A1 | 12/2014 | Brand | |
| 2015/0073306 A1 | 3/2015 | Abeyratne | |
| 2016/0279361 A1 | 9/2016 | Melqueeny | |
| 2016/0279375 A1 | 9/2016 | DeVries | |
| 2018/0126104 A1* | 5/2018 | Kruger | A61B 5/0823 |

OTHER PUBLICATIONS

Smith, J. et al., "Cough and its Importance in COPD", International Journal of Chronic Obstructive Pulmonary Disease, 2006: 1(3), 305-314.

Lee, K.K., et al., "Cough and Sleep", Lung, Jan. 2010, vol. 188, Supp 1, pp. : 91-94.

Larson, E.C. et al., "Accurate and Privacy Preserving Cough Sensing Using a Low-Cost Microphone", UbiComp, Proceedings of the 13th International Conference on Ubiquitous Computing, pp. 375-384, Sep. 2011.

O'Conner, M.C. et al., "A Wearable that Listens for Troubling Coughs", RFID Journal, Jul. 2016.

Cheung, A.P.S. et al., "Home Noninvasive Ventilation in COPD", Breathe, Mar. 2010, vol. 6, No. 3, pp. 261-266.

Drugman, T. et al., "Objective Study of Sensor Relevance for Automatic Cough Detection", Journal of Latex Class Files, vol. 6, No. 1, Jan. 2007, pp. 1-8.

Mahmoudi S.A. et al., "Sensor-Based System for Automatic Cough Detection and Classification", ICT Innovations 2015 Web Proceedings, pp. 270-279, Conference: 8th ICT Innovations Conference 2016. ELEMENT 2015—Enhanced Living EnvironMENTs, At Macedonia.

McGuinness, K. et al., "P159 Validation of the VitaloJAK 24 Hour Ambulatory Cough Monitor", BMJ Journals, Thorax, vol. 67, Issue Supl 2, Dec. 2012.

World Health Organization, "Chronic Obstructive Pulmonary Disease Fact Sheet", Nov. 2016 http://www.who.int/mediacentre/factsheets/fs315/en/.

McIntyre, N., et al., "Acute Exacerbations and Respiratory Failure in Chronic Obstructive Pulmonary Disease", Proceedings of the American Thoracic Society, vol. 5, No. 4, May 1, 2008, pp. 530-535.

Kessler, R. et al., "Symptom Variability in Patients with Severe COPD: a Pan-European Cross-Sectional Study.", European Respiratory Journal, 2011; vol. 37, No. 2, pp. 264-272.

De Oliveira JC., et al., "Clinical Significance in COPD Patients Followed in a Real Practice", Multidisciplinary Respiratory Medicine, 2013, vol. 8, No. 43, pp. 1-6.

* cited by examiner

COUGH DETECTION IN A RESPIRATORY SUPPORT SYSTEM

CROSS-REFERENCE TO RELATED APPLICATIONS

This patent application claims the priority benefit under 35 U.S.C. § 119(e) of U.S. Provisional Application No. 62/587,602, filed on Nov. 17, 2017, the contents of which are herein incorporated by reference.

BACKGROUND OF THE INVENTION

1. Field of the Invention

The present disclosure pertains to a cough detection system configured to detect respiratory events based on signals from sensors within the cough detection system.

2. Description of the Related Art

Chronic obstructive pulmonary disease (COPD) is a progressive, life threatening lung disease primarily related to exposure to tobacco smoke that causes breathlessness and predisposes the sufferer to exacerbations and serious illness. COPD is associated with progressive, irreversible worsening of airflow limitation secondary to alveolar wall destruction, bronchiolar narrowing, and airway inflammation. Cough is considered an important biomarker of changes in respiratory baseline status for COPD patients.

Various techniques for the clinical assessment of cough are known, however they are each subject to limitations. They include subjective patient reporting via questionnaires, labor intensive manual cough counting by trained observers, and microphone-based wearable cough monitors that use automated algorithms and digital signal processing to detect and report cough episodes and are inherently subject to noise artifacts, interference, and user error.

SUMMARY OF THE INVENTION

Accordingly, one or more aspects of the present disclosure relate to a system for cough detection that may, for instance, be incorporated into a respiratory pressure support or ventilation system. The cough detection system comprises a pressure generator, one or more sensors, one or more processors, and/or other components. The pressure generator is configured to generate a pressurized flow of breathable gas for delivery to the airway of a subject. The one or more sensors are configured to generate output signals conveying information related to one or more parameters of the pressurized flow of breathable gas. The one or more processors are configured to execute computer program components. The computer program components may include a gas parameter component configured to determine the one or more parameters of the pressurized flow of breathable gas based at least in part on the output signals of the sensors, wherein the one or more parameters include a pressure signal as a function of time, and a breathing parameter component configured to determine one or more breathing parameters of a subject. The computer program components may also include a cough detection component configured to detect a respiratory event based at least in part on a fluctuation in the pressure signal and/or other components. The fluctuation may include a plurality of peak pressure signal values and a plurality of valley pressure values, wherein at least one adjacent pair of peaks is separated by a time interval that is no greater than a peak pressure interval threshold, and a peak-to-valley amplitude of an adjacent peak and valley pair is no less than a pressure fluctuation amplitude threshold. The cough detection component may be configured to detect and/or corroborate a respiratory event based on a pressure signal fluctuation meeting criteria defined with the peak pressure interval threshold and/or pressure fluctuation amplitude threshold values. The cough detection component may be further configured to detect and/or corroborate a respiratory event based on other gas parameters meeting criteria that may be defined with other threshold values.

Another aspect of the present disclosure relates to a method for detecting a respiratory event with a cough detection system. The cough detection system comprises a pressure generator, one or more sensors, one or more processors, and/or other components. The one or more processors are configured to execute computer program components. The computer program components comprise a gas parameter component, a breathing parameter component, a cough detection component, a control component, and/or other components. The method comprises generating a pressurized flow of breathable gas for delivery to the airway of a subject with the pressure generator; generating output signals conveying information related to one or more parameters of the pressurized flow of breathable gas with the one or more sensors; determining the one or more parameters of the pressurized flow of breathable gas with the gas parameter component, wherein the determination is based at least in part on the generated output signals, and wherein the one or more parameters include a pressure signal; and determining a respiratory event with the cough detection component based at least in part on a fluctuation in the pressure signal including a plurality of peak pressure values and a plurality of valley pressure values, wherein at least one adjacent pair of peaks is separated by a time interval that is no greater than a peak pressure interval threshold, and wherein a peak-to-valley amplitude of an adjacent peak and valley pair is no less than a pressure fluctuation amplitude threshold.

Still another aspect of present disclosure relates to a cough detection system for detecting a respiratory event. The cough detection system comprises means for generating a pressurized flow of breathable gas for delivery to the airway of a subject; means for generating output signals conveying information related to one or more parameters of the pressurized flow of breathable gas; and means for executing computer program components. The computer program components comprise means for determining the one or more parameters of the pressurized flow of breathable gas, wherein the determination is based at least in part on the output signals, and wherein the one or more parameters include a pressure signal; and means for determining the respiratory event, wherein the respiratory event is determined based at least in part on a fluctuation in the pressure signal, the fluctuation including a plurality of peak pressure values and a plurality of valley pressure values, and wherein at least one adjacent pair of peaks is separated by a time interval that is no greater than a peak pressure interval threshold and a peak-to-valley amplitude of an adjacent peak and valley pair is no less than a pressure fluctuation amplitude threshold.

These and other objects, features, and characteristics of the present disclosure, as well as the methods of operation and functions of the related elements of structure and the combination of parts and economies of manufacture, will become more apparent upon consideration of the following description and the appended claims with reference to the accompanying drawings, all of which form a part of this specification, wherein like reference numerals designate corresponding parts in the various figures. It is to be expressly understood, however, that the drawings are for the purpose of illustration and description only and are not intended as a definition of the limits of the disclosure.

DETAILED DESCRIPTION OF EXEMPLARY EMBODIMENTS

Figure 1:
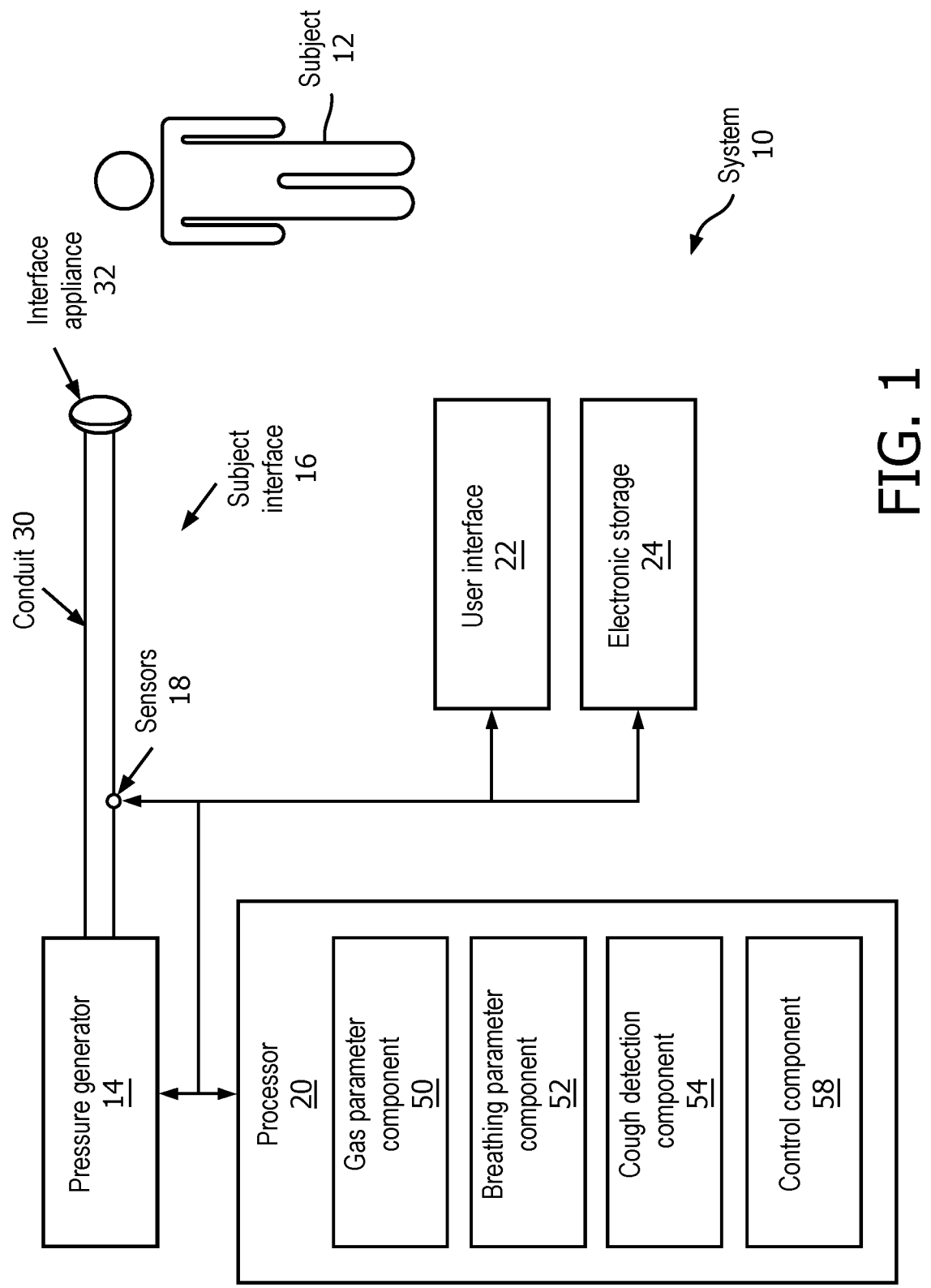
FIG. 1 is a schematically illustrates a cough detection system configured to detect a respiratory event of a subject.

As used herein, the singular form of "a", "an", and "the" include plural references unless the context clearly dictates otherwise. As used herein, the statement that two or more parts or components are "coupled" shall mean that the parts are joined or operate together either directly or indirectly, i.e., through one or more intermediate parts or components, so long as a link occurs. As used herein, "directly coupled" means that two elements are directly in contact with each other. As used herein, "fixedly coupled" or "fixed" means that two components are coupled so as to move as one while maintaining a constant orientation relative to each other.

As used herein, the word "unitary" means a component is created as a single piece or unit. That is, a component that includes pieces that are created separately and then coupled together as a unit is not a "unitary" component or body. As employed herein, the statement that two or more parts or components "engage" one another shall mean that the parts exert a force against one another either directly or through one or more intermediate parts or components. As employed herein, the term "number" shall mean one or an integer greater than one (i.e., a plurality).

Directional phrases used herein, such as, for example and without limitation, top, bottom, left, right, upper, lower, front, back, and derivatives thereof, relate to the orientation of the elements shown in the drawings and are not limiting upon the claims unless expressly recited therein.

FIG. 1 is a schematic illustration of an embodiment of a cough detection system 10 that may include, for instance, on a respiratory support apparatus or ventilator system. System 10 is configured to control the pressure support to generate a flow of breathable gas for delivery to the airway of the subject 12. In some embodiments, system 10 includes one or more of a pressure generator 14, a subject interface 16, one or more sensors 18, a processor 20, a user interface 22, electronic storage 24, and/or other components. Respiratory events may be detected based on parameters derived from output signals from sensors 18. Parameters may be measured as a function of time, and may include a pressure signal, a patient flow, a patient lung volume and/or other parameters of the pressurized flow of breathable gas. In some embodiments, a respiratory event may be detected based on an aspect and/or feature of the pressure signal. In some embodiments, a respiratory event detected based on the pressure signal may be confirmed and/or corroborated based on aspects and/or features of the patient flow, patient lung volume and/or other parameters of the pressurized flow of breathable gas.

COPD patients are commonly treated using respiratory support apparatus and/or therapy regimes such as continuous positive airway pressure (CPAP), auto CPAP (APAP), bi-level positive airway pressure support (BiPAP®), and/or other modes of noninvasive ventilation (S/T, PC, AVAPS-AE, etc.). System 10 is configured to provide such support, and also to monitor one or more parameters of the pressurized flow of breathable gas. System 10 is further configured to detect and monitor respiratory events including patient cough as an indication of overall respiratory status, as well as to specifically identify changes in respiratory status for the purpose of acute exacerbation of chronic obstructive pulmonary disease (AECOPD) risk stratification, for example. The average patient with COPD experiences two AECOPD events annually accounting for a significant consumption of health care resources. An AECOPD event has been described as a clinical diagnosis that is made when a patient with COPD fits one or more of the following criteria: sustained (e.g., 24-48 hour) increase in cough, sputum production, and/or dyspnea. AECOPD is associated with a wide range of clinical consequences including progressive respiratory failure.

Cough and sputum production are reported by between 60-80% of patients with COPD, and chronic cough and mucus hypersecretion are associated with accelerated lung function decline, increased exacerbation rate and increased mortality in COPD. Cough is known to be blunted during sleep, though the exact reasons are not fully understood. Nocturnal coughing can be an indication of sleep fragmentation which is also important in the evaluation and monitoring of COPD, as both sleep and cough are vital functions. Studies of the predictive value of respiratory symptoms including cough and sputum production for hospitalization have shown that cough has the greatest predictive value for subsequent hospital admission due to respiratory disease and COPD. Therefore, system 10 is configured to use monitored parameters of the pressurized flow of breathable gas during sleep and/or at other times, to discreetly detect and monitor respiratory events. Accordingly, a novel method of extracting and processing a pressure signal, for instance, from a positive pressure sleep therapy/non-invasive ventilation platform with a nasal or nasal/oral mask interface, is disclosed. This signal can be used to track and analyze respiratory events and as well as deviations from baseline averages as an indication of overall respiratory status. In some embodiments, the information thereby obtained can be used to specifically identify changes in respiratory status for the purpose of AECOPD risk stratification.

Figure 2:
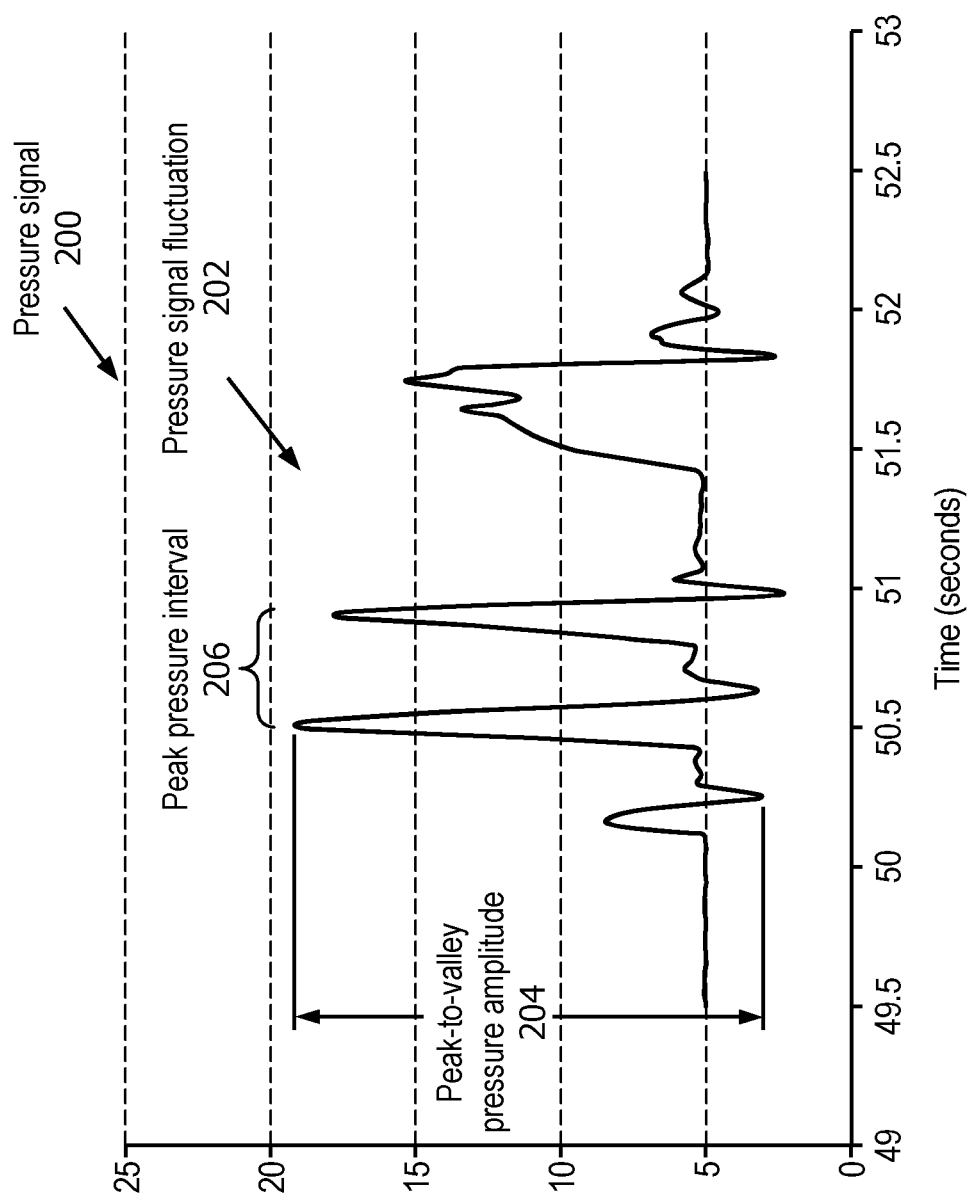
FIG. 2 shows a pressure signal with a fluctuation characteristic of a respiratory event such as a cough.

For example, FIG. 2 shows a non-limiting example of a pressure signal 200 over a period of time of approximately 12 seconds. During normal respiration, the pressure signal may be primarily attributed to pressure provided by pressure generator 14 (shown in FIG. 1). System 10 (FIG. 1) may be configured to detect a respiratory event responsive to the pressure signal being caused to deviate from the pressure controlled by generator 14 due to the forcible modification of the pressure in the system caused by a cough. For example, in some embodiments, system 10 is configured to determine that the fluctuations 202 occurring during the time interval of approximately 50 to 52 seconds may indicate that a cough occurred during that time. In some embodiments, system 10 is configured such that a pressure fluctuation is characterized by local maxima and local minima in the pressure signal over a finite time period ("peak pressures"

and "valley pressures", respectively) and/or a pressure fluctuation amplitude 204 defined by the difference between the pressure values of an adjacent peak and valley pair. In some embodiments, system 10 is configured such that a pressure signal fluctuation may further be characterized by an indicator as to how frequently the pressure signal fluctuates, such as a time interval between pressure peaks, for example peak pressure interval 206; an interval between pressure valleys; an interval between an adjacent peak and valley pair; an interval between zero pressure values; and/or other indicators. In some embodiments, a pressure fluctuation associated with a respiratory event may be further indicated or detected by a peak pressure interval time that is no greater than a peak pressure interval threshold and/or a peak-to-valley amplitude that is no less than a pressure fluctuation amplitude threshold.

Returning to FIG. 1, in some embodiments, as described above, system 10 comprises one or more of a pressure generator 14, a subject interface 16, one or more sensors 18, a processor 20, a user interface 22, electronic storage 24, and/or other components.

Pressure generator 14 is configured to generate a pressurized flow of breathable gas for delivery to the airway of subject 12. Pressure generator 14 may control one or more parameters of the flow of gas (e.g., pressure, flow rate, volume, temperature, duration, a timing, gas composition, etc.) for therapeutic purposes, and/or for other purposes.

Pressure generator 14 receives a flow of gas from a gas source, such as the ambient atmosphere, and elevates and/or reduces the pressure of that gas for delivery to the airway of a patient. Pressure generator 14 is any device, such as, for example, a pump, blower, piston, or bellows, that is capable of elevating and/or reducing the pressure of the received gas for delivery to a patient. Pressure generator 14 may comprise one or more valves for controlling the pressure and/or flow of gas, for example. Examples of a pressure generator may include some or all components of a ventilation platform, oxygen concentrator, or pressure support system. The present disclosure also contemplates controlling the operating speed of the blower, either alone or in combination with such valves, to control the pressure and/or flow of gas provided to the patient.

Subject interface 16 is configured to deliver the pressurized flow of breathable gas to the airway of subject 12. As such, subject interface 16 comprises conduit 30, interface appliance 32, and/or other components. Conduit 30 is configured to convey the pressurized flow of gas to interface appliance 32. Conduit 30 may be a flexible length of hose, or other conduit, that places interface appliance 32 in fluid communication with pressure generator 14. Interface appliance 32 is configured to deliver the flow of gas to the airway of subject 12. In some embodiments, interface appliance 32 is non-invasive. As such, interface appliance 32 non-invasively engages subject 12. Non-invasive engagement comprises removably engaging an area (or areas) surrounding one or more external orifices of the airway of subject 12 (e.g., nostrils and/or mouth) to communicate gas between the airway of subject 12 and interface appliance 32. Some examples of non-invasive interface appliance 32 may comprise, for example, a nasal cannula, a nasal mask, a nasal/oral mask, a full face mask, a total face mask, or other interface appliances that communicate a flow of gas with an airway of a subject. The present disclosure is not limited to these examples, and contemplates delivery of the flow of gas to the subject using any interface appliance, including an invasive interface appliance such as an endotracheal tube and/or other appliances.

Sensors 18 are configured to generate output signals conveying information related to one or more gas parameters of the pressurized flow of breathable gas. Such information may include, for example pressure, flow rate, temperature, etc. Sensors 18 are further configured to generate output signals conveying information related to one or more breathing parameters related to the respiration of subject 12. The one or more gas parameters and/or the one or more breathing parameters derived at least in part from information conveyed by the sensor output signals may comprise one or more of a pressure signal, a patient flow rate, a patient lung volume, a composition (e.g., concentration(s) of one or more constituents), temperature, humidity, acceleration, velocity, acoustics, changes in a parameter indicative of respiratory effort by subject 12, a timing, a duration, a frequency, and/or other parameters. Sensors 18 may comprise one or more sensors that measure such parameters directly (e.g., through fluid communication with the flow of gas in subject interface 16). Sensors 18 may comprise one or more sensors that generate output signals related to one or more parameters of the flow of gas indirectly. For example, one or more of sensors 18 may generate an output based on an operating parameter of pressure generator 14 (e.g., a valve driver or motor current, voltage, rotational velocity, and/or other operating parameters). Although sensors 18 are illustrated at a single location within (or in communication with) conduit 30 between interface appliance 32 and pressure generator 14, this is not intended to be limiting. Sensors 18 may include sensors disposed in a plurality of locations, such as for example, within pressure generator 14, within (or in communication with) interface appliance 32, in communication with subject 12, and/or in other locations. By way of non-limiting example, sensors 18 may include a pressure sensor with output signals from which a pressure signal parameter may be determined. In some embodiments, sensors 18 may include a flow sensor with output signals from which at least one of a patient flow parameter and a patient lung volume parameter may be determined.

Processor 20 is configured to provide information processing capabilities in system 10. As such, processor 20 may comprise one or more of a digital processor, an analog processor, and a digital circuit designed to process information, an analog circuit designed to process information, a state machine, and/or other mechanisms for electronically processing information. Although processor 20 is shown in FIG. 1 as a single entity, this is for illustrative purposes only. In some implementations, processor 20 may comprise a plurality of processing units. These processing units may be physically located within the same device (e.g., pressure generator 14), or processor 20 may represent processing functionality of a plurality of devices operating in coordination.

As shown in FIG. 1, processor 20 is configured to execute one or more computer program components. Computer program components may include machine-readable readable instructions, software code, code modules, routines, subroutines and/or other components configured to cause a processor to execute one or more functions. The one or more computer program components may comprise one or more of a gas parameter component 50, a breathing parameter component 52, a cough detection component 54, a control component 58, and/or other components. Processor 20 may be configured to execute components 50, 52, 54 and/or 58 by software; hardware; firmware; some combination of software, hardware, and/or firmware; and/or other mechanisms for configuring processing capabilities on processor 20.

It should be appreciated that although components 50, 52, 54, and 58 are illustrated in FIG. 1 as being co-located within a single processing unit, in implementations in which processor 20 comprises multiple processing units, one or more of components 50, 52, 54, and/or 58 may be located remotely from the other components. The description of the functionality provided by the different components 50, 52, 54, and/or 58 described below is for illustrative purposes, and is not intended to be limiting, as any of components 50, 52, 54, and/or 58 may provide more or less functionality than is described. For example, one or more of components 50, 52, 54, and/or 58 may be eliminated, and some or all of its functionality may be provided by other components 50, 52, 54, and/or 58. As another example, processor 20 may be configured to execute one or more additional components that may perform some or all of the functionality attributed below to one of components 50, 52, 54, and/or 58.

Gas parameter component 50 is configured to determine one or more gas parameters of the pressurized flow of breathable gas. Gas parameter component 50 is configured to determine the one or more gas parameters based on the output signals of sensors 18 and/or other information. The one or more gas parameters of the pressurized flow of breathable gas may comprise, for example, one or more of a pressure signal, a patient flow rate, a patient lung volume, humidity, temperature, acceleration, velocity, and/or other gas parameters. By way of non-limiting example, gas parameter component 50 may determine a pressure signal parameter by causing a processor to perform mathematical operations on output signals generated by a pressure sensor, and/or to process other sensor output signals. In some embodiments, gas parameter component 50 may determine at least one of a patient flow parameter and a patient lung volume based on output signals from a flow sensor and/or other sensor output signals. The parameters determined by gas parameter component 50 from the sensor output signals, for example, may exhibit features such as local maximum values ("peaks"), local minimum values ("valleys"), slopes, plateaus, fluctuations, frequency, periodicity, and so forth that may be used in respiratory event detection or corroboration. The information determined by gas parameter component 50 may be used for controlling pressure generator 14, determining breathing parameters of subject 12, and/or other uses.

Breathing parameter component 52 is configured to determine one or more breathing parameters of subject 12. The one or more breathing parameters are determined based on the output signals of sensors 18, information determined by gas parameter component 50, and/or based on other information. The breathing parameters may indicate a respiratory effort of subject 12 and/or other information. This includes one or more of a thoracic respiratory effort, an abdominal respiratory effort, and/or other parameters indicating respiratory effort. The one or more breathing parameters may include, for example, a tidal volume, a composition, a timing (e.g., beginning and/or end of inhalation, beginning and/or end of exhalation, etc.), a duration (e.g., of inhalation, of exhalation, of a single breathing cycle, etc.), a breath rate, a respiration frequency, and/or other parameters.

In some embodiments, breathing parameter component 52 is configured to determine one or more baseline levels of the one or more breathing parameters. The one or more baseline levels of the one or more breathing parameters may be related to normal respiration of subject 12 and/or other baseline information. In some embodiments, breathing parameter component 52 determines the one or more baseline levels of the one or more breathing parameters based on previous respiration by subject 12 and/or other information. By way of a non-limiting example, breathing parameter component 52 may determine at least one baseline level of at least one breathing parameter for individual inhalations in a series of consecutive inhalations. The at least one determined breathing parameter may include, for instance, a tidal volume, and/or other breathing parameters. Breathing parameter component 52 may determine a baseline tidal volume level for individual inhalations. By way of another non-limiting example, breathing parameter component 52 may determine at least one breathing parameter for a series of consecutive inhalations in addition to the breathing parameter determined for the individual inhalations in the series. For example, breathing parameter component 52 may determine an average tidal volume for individual inhalations in a series of consecutive inhalations. Breathing parameter component 52 may determine an average baseline tidal volume level for the series of consecutive inhalations.

Cough detection component 54 is configured to detect a respiratory event. Respiratory events include events indicated by detectable changes in features of parameters of the flow of breathable gas. Such features may include, for example, disruptions or fluctuations in the pressure signal, patient flow, patient lung volume and/or other features of those or other parameters. Respiratory events may be detected based on the output signals of sensors 18, information determined by gas parameter component 50, information determined by breathing parameter component 52, and/or based on other information. In some embodiments, the detection of respiratory events by cough detection component 54 comprises counting or assessing the frequency of coughs and/or other respiratory events over an interval of time. In some embodiments, the detection of respiratory events by cough detection component 54 is used for the purpose of AECOPD risk stratification. It should also be appreciated that the scope of the invention is not limited to cough detection, and contemplates using the system to detect other respiratory events, for instance hiccups, sneezes, apnea, dyspnea, etc.

In some embodiments the cough detection component 54 may be configured to detect or determine a respiratory event (e.g., based on pressure signal fluctuation) in a cough detection system 10 configured with components of a ventilation platform or pressure support system. Such a configuration facilitates objective, discreet cough monitoring of the subject 12 in the ordinary course of medical treatment. In some embodiments, the cough detection component 54 may be configured to detect a respiratory event based on information which may comprise one or more gas parameters (e.g. pressure signal, patient flow, patient lung volume, and/or other gas parameters), one or more breathing parameters (e.g., a tidal volume, a composition, a timing, a duration, a breath rate, peak flow, airway pressure, and/or other breathing parameters), and/or other information. In some embodiments, the cough detection component 54 may be configured to detect a respiratory event based on aspects or features of output signals and/or gas parameters that indicate, for example, a fluctuation in the pressure signal, a cessation in patient flow and/or large insufflation prior to the respiratory event, and/or a significant negative spike in patient flow indicating a sudden, strong exhalation substantially concurrent with a pressure fluctuation. The presence of these features may distinguish a cough from other perturbations in pressure caused by for example, snores, throat clearance or speaking. The foregoing examples are not intended to be limiting, as any number of techniques for detecting a respiratory event could be implemented without departing from the scope of this disclosure.

Figure 3A:
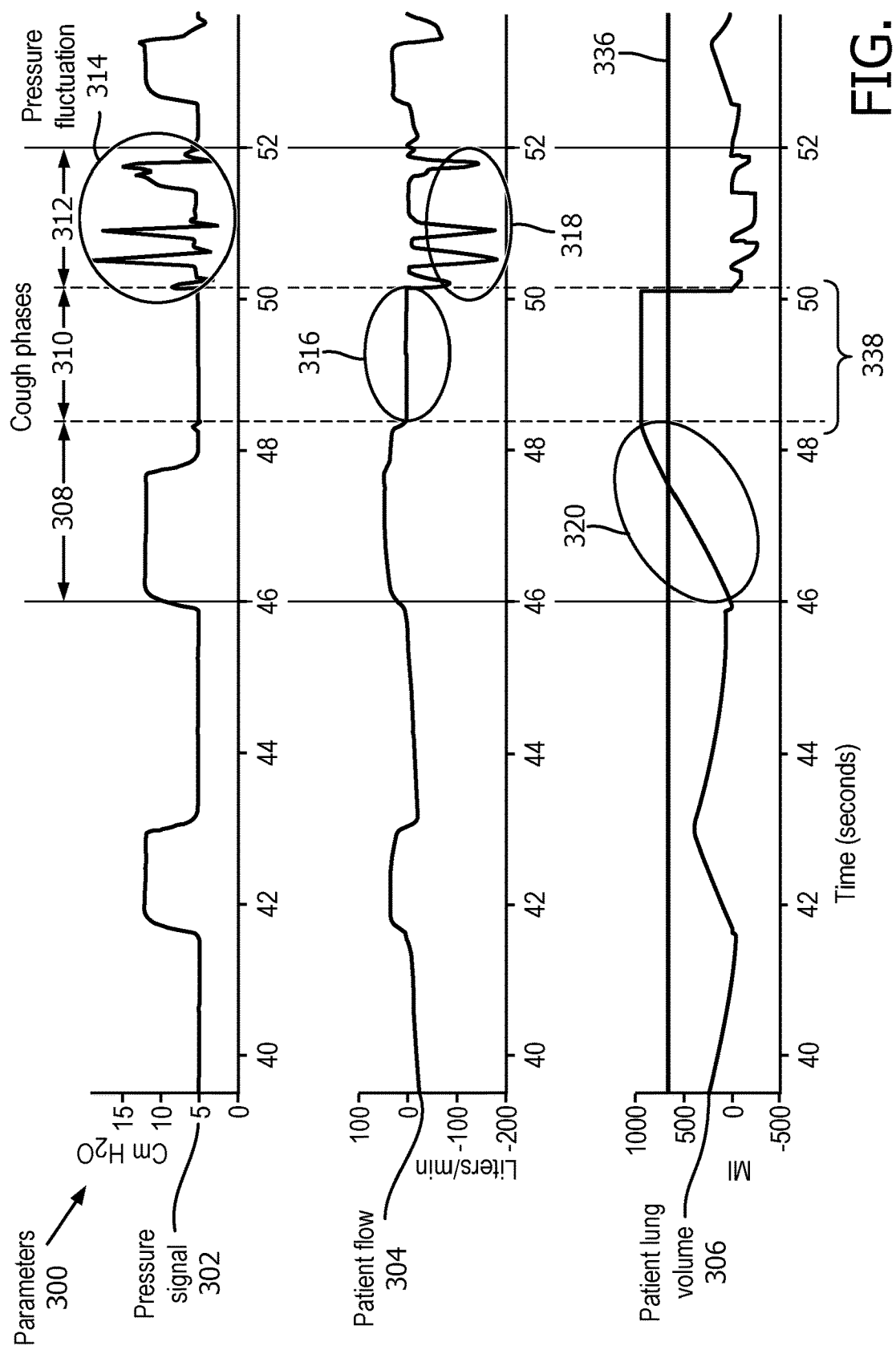
FIGS. 3A-3C illustrates the use of various parameters of the pressurized flow of breathable gas to detect and corroborate the determination of a cough.

For example, FIG. 3A illustrates aspects of some of the gas parameters 300 that could be used (e.g., by cough detection component 54 shown in FIG. 1) to determine a respiratory event, for instance a cough, alone or in combination, in various embodiments. The pressure signal 302, patient flow 304, and patient lung volume 306 associated with a period of time including one or more coughs occurring between approximately 45 and 52 seconds are shown. In some embodiments, cough detection is based on the phases 308, 310, and 312 of a cough shown superimposed on the gas parameters 300, and/or based on other information. Typically, phase one 308 of the cough begins with an insufflation during which air rushes into and fills the lungs. Phase two 310 is the compressive phase during which the glottis closes, airflow essentially ceases, and the chest contracts against the closed glottis raising intrathoracic pressure to a maximum level. Phase three 312 is the explosive phase, occurring as the maximal pressure forces the glottis open allowing the sudden expulsion of air. When this expulsion occurs during a time when a patient is using the pressure support system shown in FIG. 1 including a pressure generator 14 such as a mechanical ventilator, pressure control provided by control component 58 (shown in FIG. 1 and described below) is influenced by the cough, and the cough produces pressure fluctuations that are reflected in the output signals of one or more of the sensors 18 (FIG. 1).

Accordingly and by way of non-limiting example, in some embodiments, cough detection component 54 (FIG. 1) is configured such that a pressure signal fluctuation the same as or similar to event 314 may indicate a cough-induced fluctuation in the pressure signal 302 during phase three of a cough. Cough detection component 54 may be configured to detect a cough and/or other respiratory event based at least in part on such a pressure signal fluctuation. For example, a pressure signal fluctuation characteristic of a cough may be detected based on distinguishing aspects such as the amplitude and spacing of features of the pressure signal. For instance, the spacing between adjacent local maxima in the pressure signal curve (FIG. 2, peak pressure interval 206, for example) is much less during the pressure fluctuation interval than it is outside of that interval when the pressure signal is primarily due to the pressure provided by pressure generator 14 as determined by control component 58.

In some embodiments, cough detection component 54 (FIG. 1) is configured such that features indicative of events the same as or similar to events 316 and/or 318 of the patient flow 304 may indicate and/or corroborate the occurrence of a respiratory event, for example a cough. Cough detection component 54 may be configured to detect a cough and/or other respiratory event based at least in part on such features and/or other information. For example, a patient flow feature characteristic of a cough may be identified based on distinguishing properties such as its amplitude and temporal relation to a pressure signal fluctuation. In this example, during phase two when the glottis is closed the patient flow should be near zero, or at least relatively constant, just prior to the explosive phase three of the cough, producing a feature characteristic of flow cessation 316 occurring prior to pressure fluctuation 314 of phase three. During phase three, the exsufflation associated with the cough may typically produce a relatively high amplitude negative spike in flow indicating the sudden exhale associated with the cough, producing a characteristic feature such as 318.

In some embodiments, cough detection component 54 (FIG. 1) is configured such that features the same as or similar to event 320 of the patient lung volume 306 may indicate and/or corroborate the occurrence of a respiratory event, for example a cough. Cough detection component 54 may be configured to detect a cough and/or other respiratory event based at least in part on such features. In this example, a patient lung volume feature characteristic of a cough may be identified based on distinguishing properties such as its amplitude and temporal relation to a pressure signal fluctuation. For example, the insufflation of phase one 308 typically results in a relatively large maximum in lung volume producing a feature such as 320 occurring prior to flow cessation 316 of phase two 310.

Returning again to FIG. 1, in some embodiments, cough detection component 54 is configured to detect respiratory events based on criteria involving threshold values of one or more gas parameters, one or more breathing parameters, and/or one or more other parameters (e.g., maximum or minimum value, range, and/or duration of aspects or features of pressure signal, patient flow, and/or patient lung volume). The threshold levels may be configurable to a user (e.g., subject 12, a doctor, a caregiver, a researcher, and/or other users), predefined at manufacture, determined based on previous respiration by subject 12, and/or determined in other manners. The threshold levels may include deviations from one or more baseline levels of one or more breathing parameters determined by breathing parameter component 52, for instance tidal volume. For example, referring to FIG. 3A, the threshold 336 for determining a large insufflation 320 associated with phase one 308 of a cough may be defined relative to a baseline lung volume characteristic of the patient and/or pressure support system.

Figure 3B:
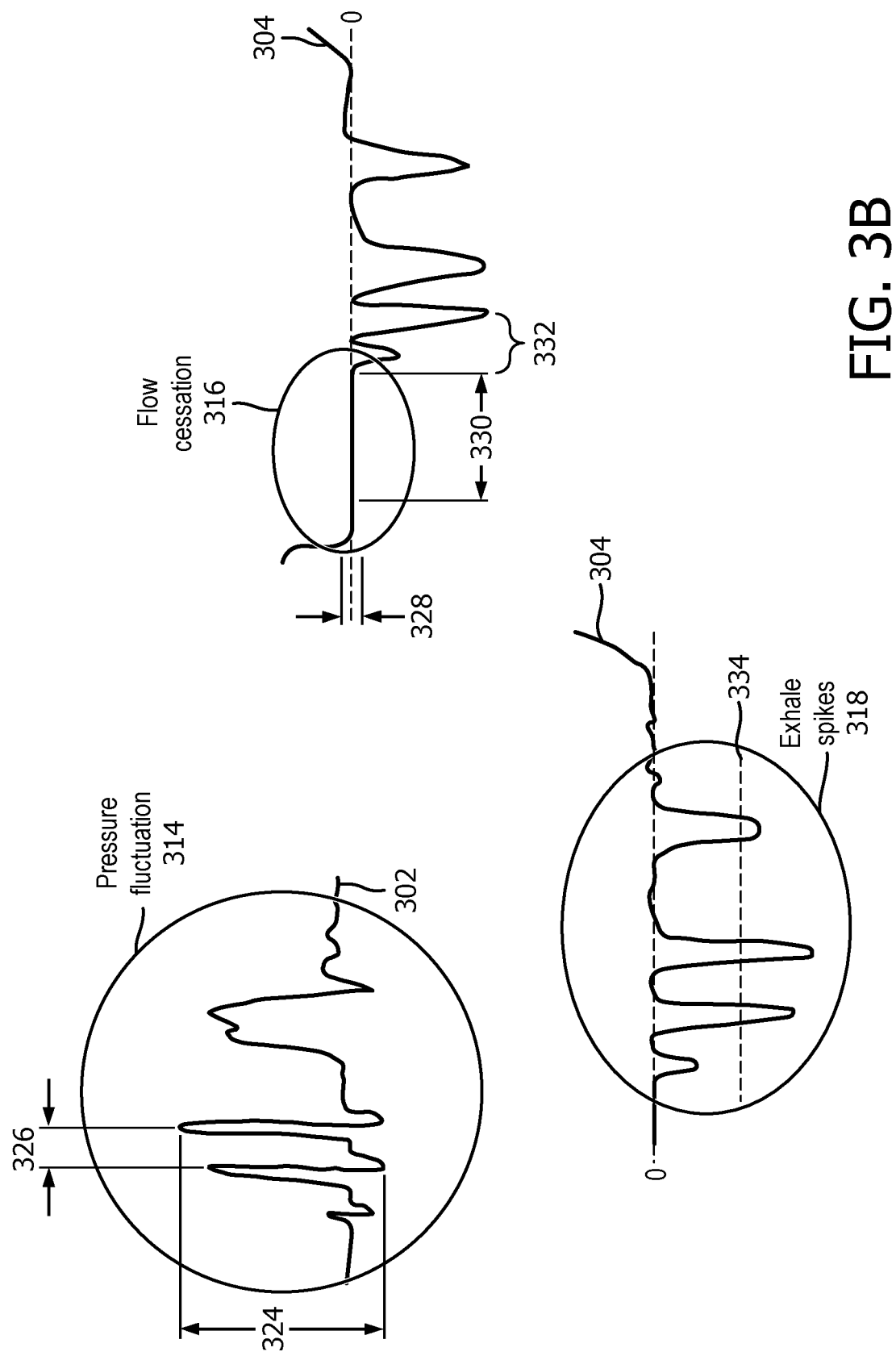

By way of a first non-limiting example, referring to FIG. 3B, a pressure fluctuation 314 may include a plurality of local maximum peak pressure values and a plurality of local minimum valley pressure values. Cough detection component 54 (FIG. 1) may be configured to detect a respiratory event based on a peak-to-valley amplitude 324 of an adjacent peak and valley pair is no less than a pressure fluctuation amplitude threshold and/or an adjacent pair of peaks being separated by a peak pressure interval 326 that is no greater than a peak pressure interval threshold. For example, the peak pressure interval threshold may be set to a value greater than a peak pressure signal interval characteristic of a cough, and less than a peak pressure interval characteristic of normal breathing. In some non-limiting embodiments, the peak pressure interval threshold may be on the order of five to eight hundred milliseconds or longer, the pressure fluctuation amplitude threshold may be on the order of four to twenty cm H2O or less, and/or the pressure fluctuation may occur primarily or entirely during phase three 312.

By way of a second non-limiting example, referring to FIG. 3A and FIG. 3B, a patient flow 304 may be characterized by amplitude that is positive when a patient is inhaling and negative when a patient is exhaling. Cough detection component 54 (FIG. 1) may be configured to detect a respiratory event based on patient flow variation (e.g., a difference between a positive peak flow a negative peak flow) of no greater than a flow variation threshold 328 for a sustained period of at least a minimum flow cessation threshold duration 330, and a delay time 332 after the temporary cessation of patient flow ends and prior to the onset of fluctuation in the pressure signal of no greater than a threshold onset delay. In some embodiments, the flow variation threshold 328 may be on the order of +/−3 liters per minute, the minimum flow cessation threshold duration 330 may be on the order of 200 milliseconds, and the threshold onset delay 332 may be on the order of 3 seconds, and/or the sustained period of at least a minimum flow cessation threshold duration may occur primarily or entirely during phase two 310.

By way of a third non-limiting example, referring again to FIG. 3A and FIG. 3B, a patient flow 304 may be characterized by amplitude that is positive when a patient is inhaling and negative when a patient is exhaling. Cough detection component 54 (FIG. 1) may be configured to detect a respiratory event based on a local minimum value of patient flow corresponding to one or more exhale spikes 318 wherein the patient flow value is below an exhale spike threshold flow level 334 and substantially concurrent with a pressure fluctuation 314. In some embodiments, the exhale spike threshold flow level 334 may be on the order of negative 30 to negative 200 liters per minute and/or the one or more exhale spikes may occur primarily or entirely during phase three indicating cough segmentation.

By way of a fourth non-limiting example, referring to FIG. 3A, a patient lung volume 306 may be characterized by amplitude that is generally greater than or equal to zero. For instance, in some embodiments, the patient lung volume may be defined in reference to a base volume, often referred to as the functional residual capacity (FRC). In such embodiments, the patient lung volume signal represents the extent to which the lung volume exceeds the baseline. During each breath the volume starts at zero (as defined by the FRC), and expands to values greater than zero during the breath before returning to zero at the start of the next breath. Irrespective of how the baseline is defined, cough detection component 54 may be configured to detect a respiratory event based on patient lung volume 306 exceeding local maximum lung volume threshold 336 corresponding to an atypically large insufflation 320 and occurring no more than a maximum insufflation threshold delay time prior 338 to the onset of fluctuations in the pressure signal. In some embodiments, the local maximum lung volume threshold 336 may be on the order of 800 milliliters, the maximum insufflation threshold delay time 338 may be on the order of a few seconds and/or the sustained period of at least a minimum flow cessation threshold duration may occur primarily or entirely during phase one 308. In some embodiments, the local maximum lung volume threshold 326 may be defined relative to a baseline level (e.g. 20% higher than normal), which in turn may be determined based on the relevant breathing history and/or breathing parameters of the subject.

Figure 3C:
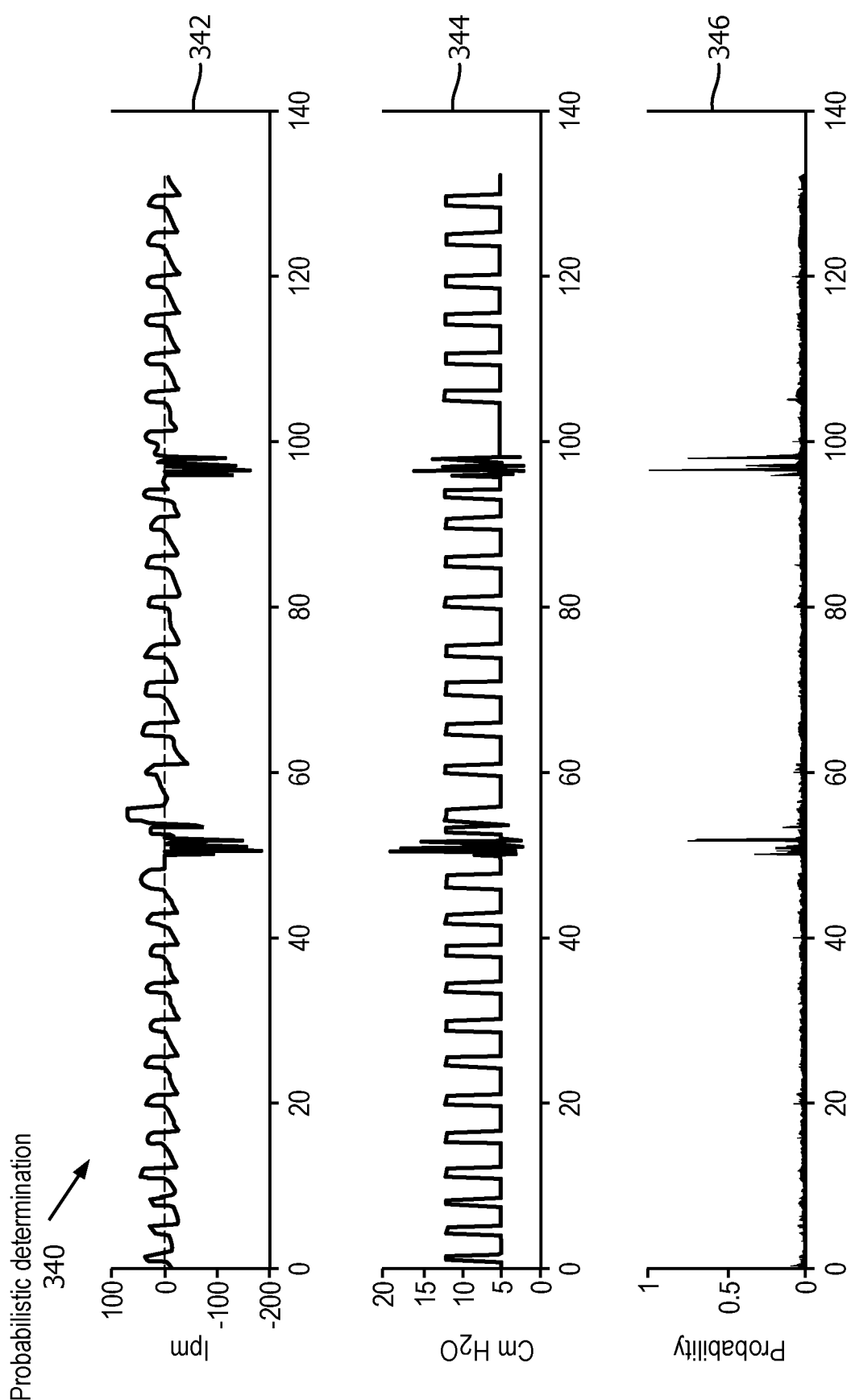

In some implementations, cough detection component 54 of system 10 may be configured to detect or determine a cough based on a probabilistic analysis. FIG. 3C illustrates the result such a determination by way of non-limiting example. In this illustration, cough detection component 54 was configured to apply a probabilistic model to patient flow 342 and pressure signal 344 parameters associated with two events, the first occurring at approximately 52 seconds and the second occurring at approximately 96 seconds, to predict the probability that a cough occurred in each instance. Pressure, flow and volume signals based at least in part on the output signals of the sensors 18 of system 10 were observed continuously. Six Boolean (true/false) predictor variables were assigned: 1. peak pressure interval qualified; 2. peak pressure amplitude qualified; 3. exhale spike amplitude qualified; 4. exhale spike interval qualified; and the true/false detection of the two corroboration conditions: 5. large insufflation (e.g. >800 ml) more than 1 second previously but not more than 10 seconds previously; and 6. flow cessation (e.g. flow <+/−3 lpm) for greater than a specified time interval ending not more than 3 seconds previously.

As a result, the states of the six Boolean variables were compared to those associated with a set of known true coughs labeled as such by trained observers, and a probability was assigned according to Bayes Theorem. As a result of the continuous true/false state of the 6 Boolean variables at these instances, cough detection module 54 determined high and very high probabilities that a cough had occurred during the time intervals near approximately 52 and 96 seconds, respectively. The probabilistic determination method set forth above is presented as an example, and the scope of the method is not limited to the use of Bayes Theorem, assignment of a plurality of Boolean variables, comparison with observations of trained observers, or any other specific aspects of the foregoing example. Alternative methods of probabilistically determining respiratory events such as, but not limited to, K means clustering, decision trees, and/or other probabilistic analysis methods are anticipated by this invention.

Control component 58 is configured to control pressure generator 14 to provide the pressurized flow of breathable gas to the airway of the subject according to a positive airway pressure support therapy regime (e.g., CPAP, APAP, BiPAP). In some embodiments, control component 58 is configured to control pressure generator 14 to provide a minimum amount of positive airway pressure support during inhalation (e.g., IPAP) and/or exhalation (e.g., EPAP). Delivering a minimum amount of pressure support may increase the comfort level of subject 12 during therapy. The minimum amount of positive airway pressure support may comprise delivering the pressurized flow of breathable gas at a minimum pressure level. In some embodiments, the minimum pressure level may be configured such that carbon dioxide re-breathing is substantially avoided during pressure support therapy.

Returning to FIG. 1, user interface 22 is configured to provide an interface between system 10 and subject 12 and/or other users through which subject 12 and/or other users may provide information to and receive information from system 10. User interface 22 may be configured to receive entry and/or selection of control inputs related to the positive airway pressure support therapy regime, the pulse parameters, and/or other information from subject 12 and/or other users. Other users may comprise a caregiver, a doctor, a decision maker, and/or other users. This enables data, cues, results, and/or instructions and any other communicable items, collectively referred to as "information," to be communicated between a user (e.g., subject 12) and one or more of pressure generator 14, processor 20, and/or other components of system 10. Examples of interface devices suitable for inclusion in user interface 22 comprise a keypad, buttons, switches, a keyboard, knobs, levers, a display screen, a touch screen, speakers, a microphone, an indicator light, an audible alarm, a printer, a tactile feedback device, and/or other interface devices. In some embodiments, user interface 22 comprises a plurality of separate interfaces. In some embodiments, user interface 22 comprises at least one interface that is provided integrally with pressure generator 14.

It is to be understood that other communication techniques, either hard-wired or wireless, are also contemplated by the present disclosure as user interface 22. For example, the present disclosure contemplates that user interface 22 may be integrated with a removable storage interface provided by electronic storage 24. In this example, information may be loaded into system 10 from removable storage (e.g., a smart card, a flash drive, an SD card, etc.) that enables the user(s) to customize the implementation of system 10. Other exemplary input devices and techniques adapted for use with system 10 as user interface 22 comprise, but are not limited to, an RS-232 port, an Ethernet port, a keyboard, a mouse, a touchpad, a voice recognition system, a gesture recognition system, RF link, an IR link, modem (telephone, cable or other). In short, any technique for communicating information with system 10 is contemplated by the present disclosure as user interface 22.

In some embodiments, electronic storage 24 comprises electronic storage media that electronically stores information. The electronic storage media of electronic storage 24 may comprise one or both of system storage that is provided integrally (i.e., substantially non-removable) with system 10 and/or removable storage that is removably connectable to system 10 via, for example, a port (e.g., a USB port, a FireWire port, etc.) or a drive (e.g., a flash drive, etc.). Electronic storage 24 may comprise one or more of optically readable storage media (e.g., optical disks, etc.), magnetically readable storage media (e.g., magnetic tape, magnetic hard drive, floppy drive, etc.), electrical charge-based storage media (e.g., EPROM, RAM, etc.), solid-state storage media (e.g., flash drive, SD card, etc.), and/or other electronically readable storage media. Electronic storage 24 may store software algorithms, information determined by processor 20, information received via user interface 22, and/or other information that enables system 10 to function properly. Electronic storage 24 may be (in whole or in part) a separate component within system 10, or electronic storage 24 may be provided (in whole or in part) integrally with one or more other components of system 10 (e.g., user interface 22, processor 20, etc.).

Figure 4:
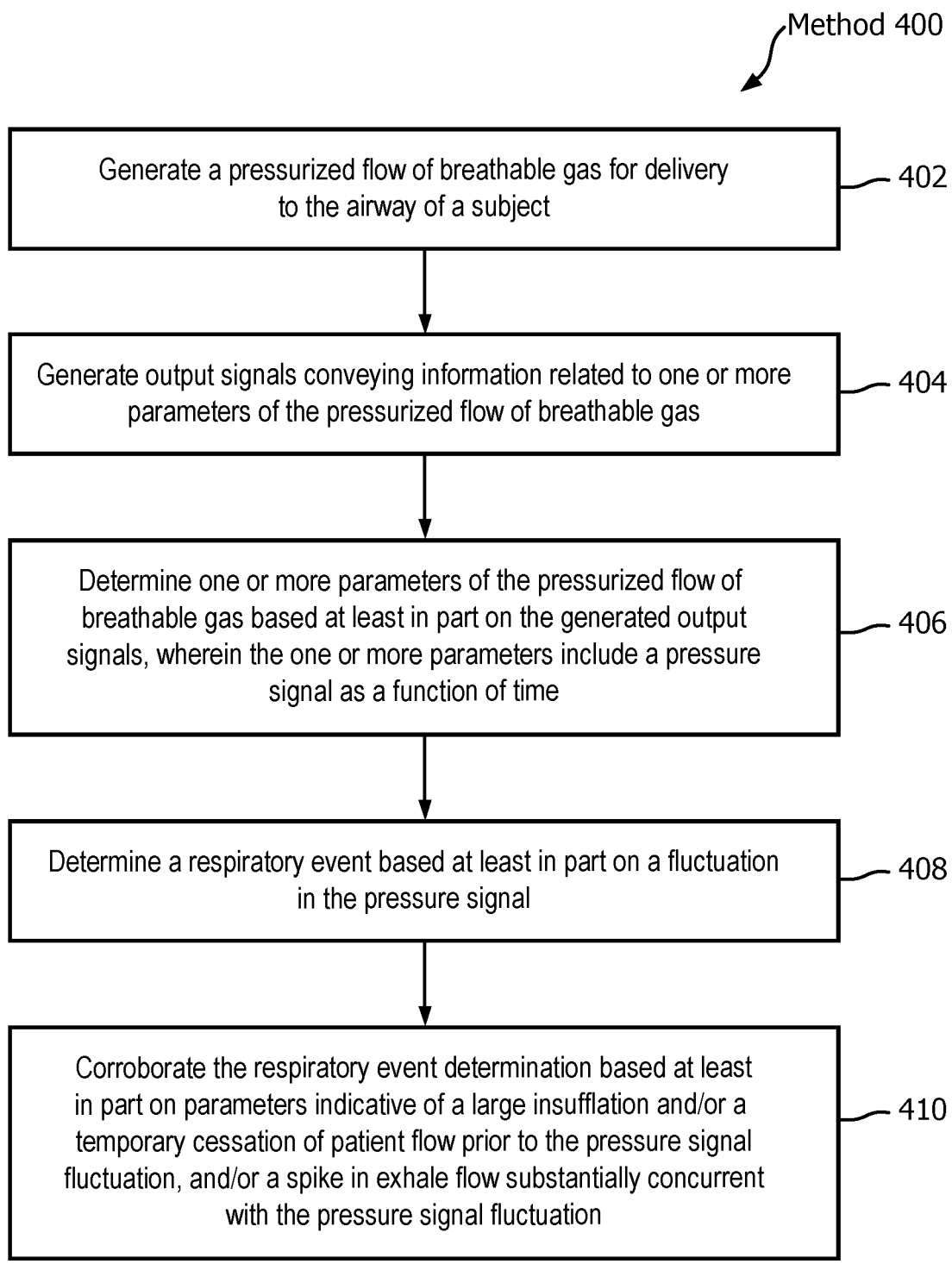
FIG. 4 illustrates a method of detecting a respiratory event of a subject using a cough detection system.

FIG. 4 illustrates a method 400 for detecting respiratory events of a subject within a pressure support system. The system comprises a pressure generator, one or more sensors, and one or more processors. The one or more processors are configured to execute computer program components. The computer program components comprise a gas parameter component, a breathing parameter component, a cough detection component, and a control component. The operations of method 400 presented below are intended to be illustrative. In some embodiments, method 400 may be accomplished with one or more additional operations not described, and/or without one or more of the operations discussed. Additionally, the order in which the operations of method 400 are illustrated in FIG. 4 and described below is not intended to be limiting.

In some embodiments, method 400 may be implemented in one or more processing devices (e.g., a digital processor, an analog processor, a digital circuit designed to process information, an analog circuit designed to process information, a state machine, and/or other mechanisms for electronically processing information). The one or more processing devices may include one or more devices executing some or all of the operations of method 400 in response to instructions stored electronically on an electronic storage medium. The one or more processing devices may include one or more devices configured through hardware, firmware, and/or software to be specifically designed for execution of one or more of the operations of method 400.

At an operation 402, a pressurized flow of breathable gas is generated for delivery to an airway of a subject. In some embodiments, operation 402 is performed by a pressure generator the same as or similar to pressure generator 14 (shown in FIG. 1 and described herein).

At an operation 404, output signals conveying information related to one or more parameters of the pressurized flow of breathable gas are generated. In some embodiments, operation 404 is performed by sensors the same as or similar to sensors 18 (shown in FIG. 1 and described herein).

At an operation 406, one or more parameters of a pressurized flow of breathable gas are determined based at least in part on the generated output signals. At an operation 406, a pressure signal parameter may be determined. At operation 406, a patient flow rate, a patient lung volume, and/or other parameters of a pressurized flow of breathable gas may be determined instead of and/or in addition to a pressure signal. In some embodiments, operation 406 is performed by a computer program component the same as or similar to gas parameter component 50 (shown in FIG. 1 and described herein).

At an operation 408, a respiratory event is determined. At an operation 408, determination of a respiratory event may be based at least in part on a fluctuation in the pressure signal. In some embodiments, the fluctuation may include a plurality of local maximum peak pressure values and a plurality of local minimum valley pressure values, wherein at least one adjacent pair of peaks is separated by a time interval that is no greater than a peak pressure interval threshold and/or a peak-to-valley amplitude of an adjacent peak and valley pair is no less than a pressure fluctuation amplitude threshold. In some embodiments, operation 408 is performed by a computer program component the same as or similar to cough detection component 54 (shown in FIG. 1 and described herein).

At an operation 410, a respiratory event determination may be corroborated using additional parameters of a pressurized flow of breathable gas. At an operation 410, a respiratory event determination may be further based on or corroborated by aspects of parameters such as a patient flow rate, a patient lung volume, and/or other parameters. In some embodiments, respiratory event determination may be based at least in part on a large insufflation and/or a temporary cessation of patient flow prior to the pressure signal fluctuation, and/or a spike in exhale flow substantially concurrent with the pressure signal fluctuation (shown in FIG. 3 and described herein). In some embodiments, the respiratory event determination may be corroborated by a computer program component the same as or similar to cough detection component 54 (shown in FIG. 1 and described herein) and/or one or more additional computer program components.

In the claims, any reference signs placed between parentheses shall not be construed as limiting the claim. The word "comprising" or "including" does not exclude the presence of elements or steps other than those listed in a claim. In a device claim enumerating several means, several of these means may be embodied by one and the same item of hardware. The word "a" or "an" preceding an element does not exclude the presence of a plurality of such elements. In any device claim enumerating several means, several of these means may be embodied by one and the same item of hardware. The mere fact that certain elements are recited in mutually different dependent claims does not indicate that these elements cannot be used in combination.

Although the description provided above provides detail for the purpose of illustration based on what is currently considered to be the most practical and preferred embodiments, it is to be understood that such detail is solely for that purpose and that the disclosure is not limited to the expressly disclosed embodiments, but, on the contrary, is intended to cover modifications and equivalent arrangements that are within the spirit and scope of the appended claims. For example, it is to be understood that the present disclosure contemplates that, to the extent possible, one or more features of any embodiment can be combined with one or more features of any other embodiment.

What is claimed is:

1. A cough detection system comprising:
a pressure generator configured to generate a pressurized flow of breathable gas for delivery to the airway of a subject;
one or more sensors configured to generate output signals conveying information related to one or more parameters of the pressurized flow of breathable gas; and
one or more processors configured to execute computer program components, the computer program components comprising:
a gas parameter component configured to determine the one or more parameters of the pressurized flow of breathable gas based at least in part on the output signals of the sensors, wherein the one or more parameters include a pressure signal, and
a cough detection component configured to determine a respiratory event based at least in part on a fluctuation in the pressure signal including a plurality of local maximum peak pressure values and a plurality of local minimum valley pressure values, wherein at least one adjacent pair of peaks is separated by a time interval that is no greater than a peak pressure interval threshold, and wherein a peak-to-valley amplitude of an adjacent peak and valley pair is no less than a pressure fluctuation amplitude threshold.

2. The system of claim 1, wherein the peak pressure interval threshold is at most one second or the pressure fluctuation amplitude threshold is at least two cm $H_2O$.

3. The system of claim 1, wherein the one or more parameters further include a patient flow as a function of time, and the cough detection component is further configured to determine a respiratory event based at least in part on a temporary cessation of patient flow indicated by:
patient flow variation of no greater than a flow variation threshold for a sustained period of at least a minimum flow cessation threshold duration; and
a delay time after the temporary cessation of patient flow ends and prior to the onset of fluctuation in the pressure signal of no greater than a threshold onset delay.

4. The system of claim 1, wherein the one or more parameters further include a patient flow as a function of time, and the cough detection component is further configured to determine a respiratory event based at least in part on a local minimum value of patient flow substantially concurrent with the fluctuation in the pressure signal and below an exhale spike threshold flow level.

5. The system of claim 1, wherein the one or more parameters further include a patient lung volume as a function of time, and the cough detection component is further configured to determine a respiratory event based at least in part on a local maximum lung volume threshold corresponding to a large insufflation and occurring no more than a maximum insufflation threshold delay time prior to the onset of fluctuations in the pressure signal.

6. A method for detecting a respiratory event with a cough detection system, the cough detection system comprising a pressure generator, one or more sensors, and one or more processors, the one or more processors configured to execute computer program components, the computer program components comprising a gas parameter component, a breathing parameter component, a cough detection component, and a control component, the method comprising:
generating a pressurized flow of breathable gas for delivery to the airway of a subject with the pressure generator;
generating output signals conveying information related to one or more parameters of the pressurized flow of breathable gas with the one or more sensors;
determining the one or more parameters of the pressurized flow of breathable gas with the gas parameter component, wherein the determination is based at least in part on the generated output signals, and wherein the one or more parameters include a pressure signal; and
determining a respiratory event with the cough detection component based at least in part on a fluctuation in the pressure signal including a plurality of local maximum peak pressure values and a plurality of local minimum valley pressure values, wherein at least one adjacent pair of peaks is separated by a time interval that is no greater than a peak pressure interval threshold, and wherein a peak-to-valley amplitude of an adjacent peak and valley pair is no less than a pressure fluctuation amplitude threshold.

7. The method of claim 6, wherein the peak pressure interval threshold is at most one second or the pressure fluctuation amplitude threshold is at least two cm $H_2O$.

8. The method of claim 6, wherein the one or more parameters further include a patient flow as a function of time, and the method further comprises determining a respiratory event based at least in part on a temporary cessation of patient flow indicated by:
patient flow variation of no greater than a flow variation threshold for a sustained period of at least a minimum flow cessation threshold duration; and
a delay time after the temporary cessation of patient flow ends and prior to the onset of fluctuation in the pressure signal of no greater than a threshold onset delay.

9. The method of claim 6, wherein the one or more parameters further include a patient flow as a function of time, and the method further comprises determining a respiratory event based at least in part on a local minimum value of patient flow substantially concurrent with the fluctuation in the pressure signal and below an exhale spike threshold flow level.

10. The method of claim 6, wherein the one or more parameters further include a patient lung volume as a function of time, and the method further comprises determining a respiratory event based at least in part on a local maximum lung volume threshold corresponding to a large insufflation and occurring no more than a maximum threshold delay time prior to the onset of fluctuations in the pressure signal.

11. A cough detection system for detecting a respiratory event, the cough detection system comprising:
means for generating a pressurized flow of breathable gas for delivery to the airway of a subject;
means for generating output signals conveying information related to one or more parameters of the pressurized flow of breathable gas; and
means for executing computer program components, the computer program components comprising:
means for determining the one or more parameters of the pressurized flow of breathable gas, wherein the determination is based at least in part on the output signals, and wherein the one or more parameters include a pressure signal; and
means for determining the respiratory event, the determination based at least in part on a fluctuation in the pressure signal including a plurality of local maximum peak pressure values and a plurality of local minimum valley pressure values, wherein at least one adjacent pair of peaks is separated by a time interval that is no greater than a peak pressure interval threshold, and wherein a peak-to-valley amplitude of an adjacent peak and valley pair is no less than a pressure fluctuation amplitude threshold.

12. The system of claim 11, wherein the peak pressure interval threshold is at most one second or the pressure fluctuation amplitude threshold is at least two cm $H_2O$.

13. The system of claim 11, wherein the one or more parameters further include a patient flow as a function of time, and the system further comprises means for determining a respiratory event based at least in part on a temporary cessation of patient flow indicated by:

patient flow variation of no greater than a flow variation threshold for a sustained period of at least a minimum flow cessation threshold duration; and a delay time after the temporary cessation of patient flow ends and prior to the onset of fluctuation in the pressure signal of no greater than a threshold onset delay.

14. The system of claim 11, wherein the one or more parameters further include a patient flow as a function of time, and the method further comprises means for determining a respiratory event based at least in part on a local minimum value of patient flow substantially concurrent with the fluctuation in the pressure signal and below an exhale spike threshold flow level.

15. The system of claim 11, wherein the one or more parameters further include a patient lung volume as a function of time, and the method further comprises means for determining a respiratory event based at least in part on a local maximum lung volume threshold corresponding to a large insufflation and occurring no more than a maximum threshold delay time prior to the onset of fluctuations in the pressure signal.

* * * * *